United States Patent
Watanabe

(10) Patent No.: US 8,496,589 B2
(45) Date of Patent: Jul. 30, 2013

(54) ULTRASONIC DIAGNOSIS DEVICE AND ULTRASONIC DIAGNOSIS SYSTEM

(75) Inventor: Yoshinobu Watanabe, Kanagawa (JP)

(73) Assignee: Panasonic Corporation, Osaka (JP)

( * ) Notice: Subject to any disclaimer, the term of this patent is extended or adjusted under 35 U.S.C. 154(b) by 500 days.

(21) Appl. No.: 12/675,288

(22) PCT Filed: Aug. 26, 2008

(86) PCT No.: PCT/JP2008/002313
§ 371 (c)(1),
(2), (4) Date: Feb. 25, 2010

(87) PCT Pub. No.: WO2009/028173
PCT Pub. Date: Mar. 5, 2009

(65) Prior Publication Data
US 2011/0112401 A1   May 12, 2011

(30) Foreign Application Priority Data
Aug. 30, 2007 (JP) .................................. 2007-223419

(51) Int. Cl.
*A61B 8/00* (2006.01)
(52) U.S. Cl.
USPC ............................. 600/443; 600/437; 600/407
(58) Field of Classification Search
USPC ................... 600/443, 437, 407; 382/154, 265, 382/305
See application file for complete search history.

(56) References Cited

U.S. PATENT DOCUMENTS

| | | | |
|---|---|---|---|
| 5,657,760 A | 8/1997 | Ying et al. | |
| 5,832,183 A * | 11/1998 | Shinohara et al. | 706/20 |
| 6,335,979 B1 * | 1/2002 | Seto et al. | 382/128 |
| 6,525,525 B1 | 2/2003 | Azinger | |
| 2004/0001080 A1 * | 1/2004 | Fowkes et al. | 345/720 |
| 2004/0186388 A1 | 9/2004 | Gerasimov | |
| 2004/0193053 A1 | 9/2004 | Kato | |
| 2005/0063575 A1 | 3/2005 | Ma et al. | |
| 2007/0230661 A1 * | 10/2007 | Motoki et al. | 378/116 |

FOREIGN PATENT DOCUMENTS

| | | |
|---|---|---|
| DE | 10118180 | 5/2002 |
| JP | 4-336053 A | 11/1992 |
| JP | 8-336529 A | 12/1996 |
| JP | 9-081646 A | 3/1997 |
| JP | 2000-152928 A | 6/2000 |
| JP | 2004-290404 | 10/2004 |
| JP | 2006-055326 A | 3/2006 |

* cited by examiner

*Primary Examiner* — Tse Chen
*Assistant Examiner* — Joel F Brutus
(74) *Attorney, Agent, or Firm* — Hamre, Schumann, Mueller & Larson, P.C.

(57) ABSTRACT

An ultrasonic diagnosis device includes a diagnostic image generation unit (7) that generates an ultrasonic image from ultrasonic data obtained by transmission and reception of ultrasonic waves; an input unit (1) for receiving an input of a reference image, and hardware configuration and control parameter information data that is associated with the reference image, which are to be used by the diagnostic image generation unit; a parameter setting unit (3) that sets parameter information necessary for generating the ultrasonic image based on the input data that has been input; and a storage unit (8) that stores the ultrasonic image in association with the parameter information, and supplies ultrasonic image data with which the parameter information is associated, as a reference image. This enables easy setting of the parameters to be used in new diagnostic image acquisition so as to be set the same as the parameters used in reference image acquisition.

4 Claims, 7 Drawing Sheets

ULTRASONIC DIAGNOSIS DEVICE AND ULTRASONIC DIAGNOSIS SYSTEM

TECHNICAL FIELD

The present invention relates to an ultrasonic diagnosis device, and in particular relates to an ultrasonic diagnosis device that stores a diagnostic image and parameters used in the generation of the diagnostic image in association with each other.

BACKGROUND ART

An ultrasonic diagnosis device is a medical imager that emits ultrasonic waves to a subject body and obtains a cross-sectional image of soft tissue based on reflected waves from tissue in the body, and ultrasonic diagnosis devices are widely used in various types of diagnosing due to their safety.

In the case of monitoring a lesion over time with use of tomographic images (hereinafter, called "diagnostic images") of soft tissue that have been acquired with an ultrasonic diagnosis device, it is possible to make a differential diagnosis as to whether, for example, the lesion has become worse than before or is getting better by comparing diagnostic images previously acquired at a site in a subject body and current diagnostic images that have been newly acquired at the same site in the same subject body, to see how the size of the displayed affected tissue or the shape of the affected margin has changed, how the brightness of the affected site relative to the peripheral tissue has changed, and so on.

In order to make such differential diagnoses reliably, the previously acquired diagnostic images and the newly-acquired current diagnostic images need to be acquired with the same image quality, and in order to achieve this, it is required for the parameters used when acquiring the previous diagnostic images and the parameters used when acquiring the new diagnostic images to be set identically. Also, it is required for such setting to be able to be performed easily and in a short amount of time in order to alleviate the burden on the operator.

An ultrasonic diagnosis device having a configuration such as shown in FIG. 7 is a known example of a conventional ultrasonic diagnosis device. In this device, a probe 30 emits ultrasonic waves based on a transmission signal from a transmission/reception unit 31, detects reflected waves, and supplies a corresponding signal to the transmission/reception unit 31. A reception signal output from the transmission/reception unit 31 is converted into a digital signal by an A/D converter 32, and a phasing and adding unit 33 performs phasing and addition on the digitized reception signal. The signal obtained by the phasing and addition is subjected to processing performed by a signal processing unit 34 and then is sent to a display image data generation unit 35, which generates display image data that then is displayed as an image by a display unit 36. The signal processing unit 34, the display image data generation unit 35, and the like are controlled by a control unit 39 that is for controlling various units. The control unit 39 is connected to an input unit 37 and a storage unit 38, and the storage unit 38 is also connected to the display image data generation unit 35.

In this ultrasonic diagnosis device, a subject body identifier, a diagnostic image, and image parameters used in diagnostic image acquisition are associated with each other and stored in the storage unit 38, and when a subject body identifier newly is input from the input unit 37, the ultrasonic diagnosis device has a function for performing a search to find out whether data related to that subject body exists in the storage unit 38. If such data exists, the diagnostic image and image parameters used in diagnostic image acquisition are readout from the storage unit 38, and the associated image parameters are set as the image parameters to be used in current diagnostic image acquisition. Then, the acquired current diagnostic image and the diagnostic image that was readout from the storage unit 38 are displayed simultaneously on the display unit 36 (e.g., see Patent Document 1).

Patent Document 1: JP 2006-55326A

DISCLOSURE OF INVENTION

Problem to be Solved by the Invention

In ultrasonic diagnosis devices, when setting the image quality parameters used in diagnostic image acquisition that are associated with the readout diagnostic image as the image quality parameters to be used in current diagnostic image acquisition, there are several hundred parameters that need to be set. For this reason, in order to set in detail to which processes in the generation of diagnostic images the parameters are to be applied in conventional ultrasonic diagnosis devices, there is the problem that unless the ultrasonic diagnosis device is the same device used when the readout diagnostic image was acquired, or has the same hardware configuration as that device, it has been difficult to re-set the device correctly using the image quality parameters used in previous diagnostic image acquisition.

The present invention has been made in order to solve such a conventional problem, and an object thereof is to provide an ultrasonic diagnosis device that extracts parameters used in acquisition of a read-out diagnostic image (hereinafter, referred to as a "reference image") from information associated with the reference image, and makes it easy to set the individual extracted parameters for the acquisition of a diagnostic image with the current hardware configuration, even if the current hardware configuration differs from that of the ultrasonic diagnosis device that acquired the reference image.

Means for Solving Problem

An ultrasonic diagnosis device according to a first configuration of the present invention includes: a diagnostic image generation unit that generates an ultrasonic image from ultrasonic data obtained by transmission and reception of ultrasonic waves; an input unit for receiving an input of data to be used by the diagnostic image generation unit; a parameter setting unit that sets parameter information necessary for generating the ultrasonic image based on the input data that has been input; and a storage unit that stores the ultrasonic image in association with the parameter information, and supplies ultrasonic image data with which the parameter information is associated, as a reference image.

This configuration enables saving an acquired ultrasonic image in association with parameters such as the setting conditions thereof, thereby enabling easy output of image data to which such parameters have been associated.

An ultrasonic diagnosis system according to a first configuration of the present invention includes an ultrasonic diagnosis device that generates a diagnostic image from ultrasonic data, and an image server that is connected to the ultrasonic diagnosis device via a communication network. The ultrasonic diagnosis device includes: a reception unit that receives, from the image server, a reference image and a hardware configuration and control parameter information that are associated with the reference image; a parameter setting unit that sets parameter information that has been converted from the information associated with the reference image into a format that is in accordance with a hardware configuration of the ultrasonic diagnosis device in order to generate a diagnostic image; an ultrasonic data acquisition unit that acquires ultrasonic data based on the parameter information set by the parameter setting unit; a diagnostic image generation unit that generates a diagnostic image by, based on the parameter information set by the parameter setting unit, performing image processing on the ultrasonic data acquired by the ultrasonic data acquisition unit; and a transmission unit that converts a change in the parameter information cause by additional adjustment into a format conforming to the hardware configuration information of the ultrasonic diagnosis device, adds the resulting information to the parameter information set by the parameter setting unit, and transmits the resulting parameter information in association with the diagnostic image generated by the diagnostic image generation unit. The image server includes: a communication unit that performs communication with the ultrasonic diagnosis device; and a storage unit that stores information.

According to this configuration, the ultrasonic diagnosis device can extract parameters used in reference image acquisition from the hardware configuration and control parameter information that are associated with the reference image and that have been received from the image server. Then, it is possible to convert the individual extracted parameters into a format that is in accordance with the hardware configuration of the ultrasonic diagnosis device, set the converted parameters as the parameters to be used in diagnostic image generation, and generate a current diagnostic image based on the set parameters. It is furthermore possible to associate the generated diagnostic image with the set parameters, which have been caused to reflect the current hardware configuration and changes in parameters caused by additional adjustment, transmit the generated diagnostic image and the set parameter to the image server via the communication network, and save them therein. This enables access from another ultrasonic diagnosis device or a medical institution that is connected to the communication network and is authorized, thus facilitating the sharing and effective utilization of data.

An ultrasonic diagnosis device according to a second configuration of the present embodiment includes a diagnostic image generation unit that generates an ultrasonic image from ultrasonic data obtained by transmission and reception of ultrasonic waves; an input unit for receiving an input of data to be used by the diagnostic image generation unit; a parameter setting unit that, when a reference image and information associated with the reference image that has been converted into control data in a certain protocol format not dependent on a hardware configuration have been input from the input unit, reproduces information associated with the reference image that has been converted into control data in the certain protocol format, extracts a parameter used in reference image acquisition from the reproduced information, and converts the extracted parameter into a format that is in accordance with hardware configuration information of the ultrasonic diagnosis device, in order to set a parameter to be used in diagnostic image generation; and an ultrasonic data acquisition unit that acquires ultrasonic data based on the parameter reproduced and set by the parameter setting unit. The diagnostic image generation unit generates a diagnostic image by, based on the parameter reproduced and set by the parameter setting unit, performing image processing on the ultrasonic data acquired by the ultrasonic data acquisition unit.

This configuration facilitates the use of a reference image and information associated with the reference image that has been converted into control data in a certain protocol format not dependent on a hardware configuration, and enables expanding the range in which the reference image is used.

An ultrasonic diagnosis system according to a second configuration of the present invention includes an ultrasonic diagnosis device that generates a diagnostic image from ultrasonic data, and an image server that is connected to the ultrasonic diagnosis device via a communication network. The ultrasonic diagnosis device includes: a reception unit that receives, form the image server, a reference image and information that is associated with the reference image and has been converted into control data in a certain protocol format not dependent on a hardware configuration; a parameter setting unit that comprises a parameter reproduction unit that reproduces the information associated with the reference image that has been converted into control data in a certain protocol format, a first parameter setting unit that sets a parameter converted into a format that is in accordance with a hardware configuration of the ultrasonic diagnosis device as a device control parameter, and a second parameter setting unit that sets a parameter as an image processing parameter; an ultrasonic data acquisition unit that acquires ultrasonic data based on parameter information set by the parameter setting unit; a diagnostic image generation unit that generates a diagnostic image by, based on the parameter information set by the parameter setting unit, performing image processing on the ultrasonic data acquired by the ultrasonic data acquisition unit; and a transmission unit that converts a change in the parameter information caused by additional adjustment into a format conforming to hardware configuration information of the ultrasonic diagnosis device, adds the resulting information to the parameter information, and transmits the information relating to the diagnostic image that has been converted into control data in a certain protocol format not dependent on a hardware configuration in association with the diagnostic image generated by the diagnostic image generation unit. The image server includes: a communication unit that performs communication with the ultrasonic diagnosis device; and a storage unit that stores information.

According to this configuration, even in the case of achieving the sharing and effective utilization of data via a communication network, the ultrasonic diagnosis device facilitates the use of a reference image and information associated with the reference image that has been converted into control data in a certain protocol format not dependent on a hardware configuration, and enables expanding the range in which the reference image is used.

Effects of the Invention

An ultrasonic diagnosis device and an ultrasonic diagnosis system of the present invention enable storing an acquired ultrasonic image in association with parameters such as the setting conditions thereof, thereby enabling easy output of image data with which such parameters have been associated.

It is also possible to receive input of a reference image and a hardware configuration and control parameter information that are associated with the reference image, and the device and system facilitate processing for extracting parameters used in reference image acquisition from the information associated with the reference image that was input, converting the extracted parameters into a format that is in accordance with the configuration of hardware connected to the input unit, setting the converted parameters as the parameters to be used in the generation of a current diagnostic image, acquiring ultrasonic data based on the set parameters, and furthermore generating a current diagnostic image by performing image processing.

Accordingly, it is possible to set image parameters that are optimum for the comparison of diagnostic images by merely inputting a reference image and making a selection, thus simplifying the image parameter setting procedure and enabling the creation of appropriate diagnostic images even by those who are not diagnostic specialists.

Figure 1:
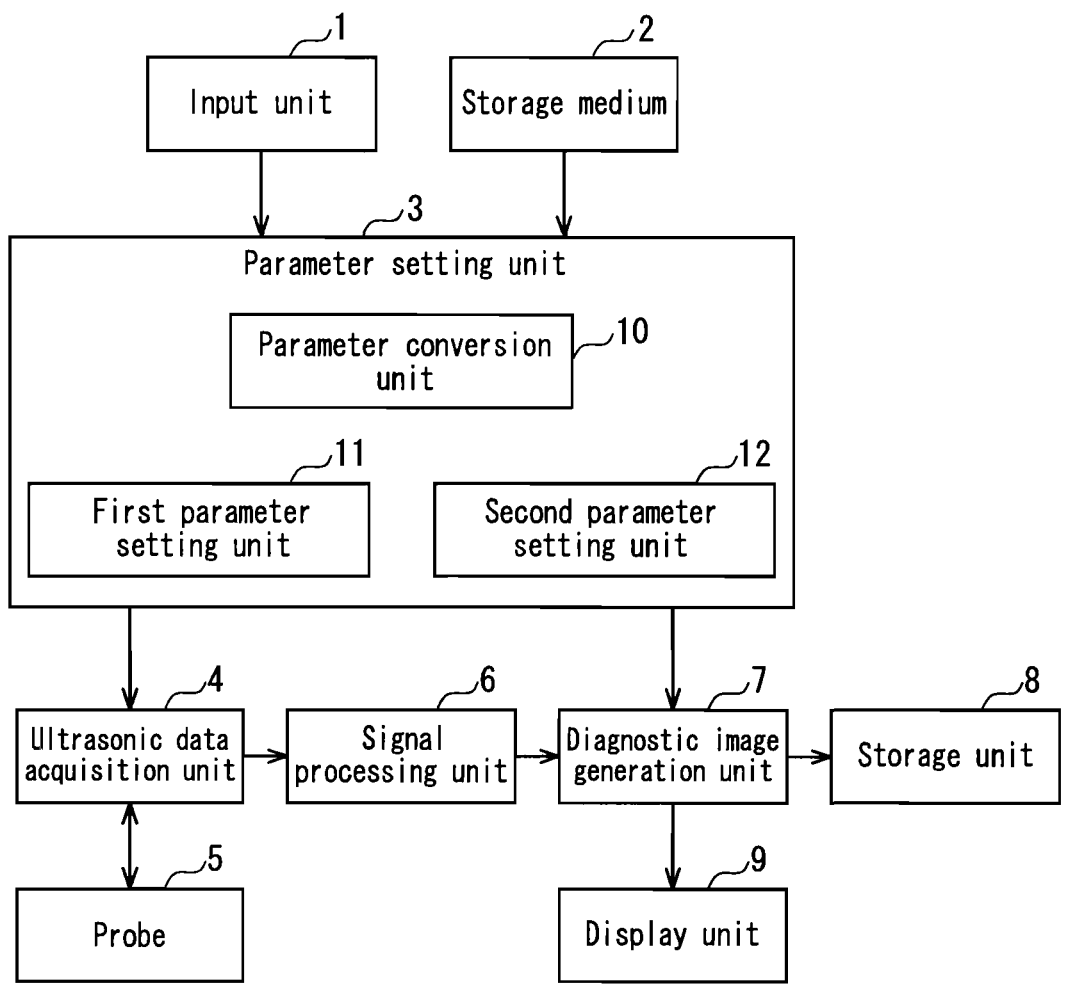
FIG. 1 is a block diagram showing a configuration of an ultrasonic diagnosis device according to Embodiment 1 of the present invention.

REFERENCE SIGNS LIST 1 input unit
2 storage medium
3, 19 parameter setting unit
4 ultrasonic data acquisition unit
5 probe
6 signal processing unit
7 diagnostic image generation unit
8, 21 storage unit
9 display unit
10 parameter conversion unit
11 first parameter setting unit
12 second parameter setting unit
13 reception unit
14, 22 transmission unit
15 communication network
16 image server
17 communication unit
18 storage unit
20 parameter reproduction unit

DESCRIPTION OF THE INVENTION

The present invention can take various forms such as the following, which are based on the above configurations.

Specifically, the ultrasonic diagnosis device according to the first configuration may include an ultrasonic data acquisition unit that, when a reference image with which parameter information is associated is input from the input unit, acquires the ultrasonic data based on the input parameter information.

Also, when a reference image with which parameter information is associated has been input from the input unit, the diagnostic image generation unit may generate a diagnostic image by performing image processing based on the parameter information that has been input.

These configurations facilitate inputting an ultrasonic image and associated parameters that are stored in another ultrasonic diagnosis device, and furthermore acquiring new ultrasonic image data with use of such parameters.

Also, it is preferable that the parameter setting unit adds hardware configuration information pertaining to the ultrasonic diagnosis device to the parameter information.

Also, the parameter setting unit may include a first parameter setting unit that sets a device control parameter based on information associated with the reference image, and a second parameter setting unit that sets an image processing parameter based on the information associated with the reference image, the ultrasonic data acquisition unit may acquire ultrasonic data based on the device control parameter set by the first parameter setting unit, and the diagnostic image generation unit may generate a diagnostic image by, based on the image processing parameter set by the second parameter setting unit, performing image processing on the ultrasonic data acquired by the ultrasonic data acquisition unit.

According to this configuration, it is possible to extract parameters used in reference image acquisition from the hardware configuration and control parameter information that are associated with the reference image, classify the individual extracted parameters into image processing parameters and device control parameters that have been converted into a format that is in accordance with the current hardware configuration, and generate a current diagnostic image by, based on the set image processing parameters, performing image processing on acquired ultrasonic data based on the set device control parameters.

Also, it is preferable that the storage unit converts a change in parameter information caused by additional adjustment into a format conforming to the hardware configuration information of the ultrasonic diagnosis device, adds the resulting information to the device control parameter set by the first parameter setting unit, and stores the resulting device control parameter and the image processing parameter set by the second parameter setting unit, in association with the diagnostic image generated by the diagnostic image generation unit.

This configuration facilitates storing the set device control parameters and the set image processing parameters that have been caused to reflect the current hardware configuration and changes in parameters caused by additional adjustment, in association with the generated diagnostic image.

Also, it is preferable that when a reference image associated with parameter information to which hardware configuration information has been added are input from the input unit, the parameter setting unit converts the input parameter information into parameter information that is in accordance with the hardware configuration of the ultrasonic diagnosis device.

This configuration enables controlling the ultrasonic diagnosis device using parameters that are in accordance with the current hardware.

Also, it is preferable that the storage unit converts a change in the parameter information caused by additional adjustment into a format conforming to the hardware configuration information of the ultrasonic diagnosis device, adds the resulting information to the parameter information set by the parameter setting unit, and stores the resulting parameter information in association with the diagnostic image generated by the diagnostic image generation unit.

This configuration facilitates storing the set parameters and the generated diagnostic image in association with each other.

In the ultrasonic diagnosis device according to the second configuration, it is preferable that the parameter setting unit includes a parameter reproduction unit that reproduces the information associated with the reference image that has been converted into control data in a certain protocol format, a first parameter setting unit that sets a parameter reproduced by the parameter reproduction unit as a device control parameter, and a second parameter setting unit that sets a parameter reproduced by the parameter reproduction unit as an image processing parameter, the ultrasonic data acquisition unit acquires ultrasonic data based on the device control parameter set by the first parameter setting unit, and the diagnostic image generation unit generates a diagnostic image by, based on the image processing parameter set by the second parameter setting unit, performing image processing on the ultrasonic data acquired by the ultrasonic data acquisition unit.

This configuration enables reproducing information associated with the reference image that has been converted into control data in a certain protocol format not dependent on the hardware configuration that has been input, extracting parameters used in reference image acquisition, classifying the individual extracted parameters into image processing parameters and device control parameters that have been converted into a format that is in accordance with the hardware configuration of the ultrasonic diagnosis device, and generating a current diagnostic image by, based on the set image processing parameters, performing image processing on the acquired ultrasonic data based on the set device control parameters.

Also, it is preferable that the ultrasonic diagnosis device includes a storage unit that converts a change in a parameter caused by additional adjustment into a format conforming to hardware configuration information of the ultrasonic diagnosis device, adds the resulting information to the information associated with the reference image that has been converted into control data in a certain protocol format, re-converts the resulting information associated with the reference image into control data in a certain protocol format not dependent on a hardware configuration, and stores the resulting control data in association with the diagnostic image generated by the diagnostic image generation unit.

This configuration enables storing the generated diagnostic image and the information associated with the reference image that has been converted into control data in a certain protocol format in association with each other.

The following describes an ultrasonic diagnosis device according to embodiments of the present invention with reference to the drawings.

Embodiment 1

FIG. 1 is a block diagram showing a configuration of an ultrasonic diagnosis device according to Embodiment 1 of the present invention. This ultrasonic diagnosis device includes an input unit 1, a parameter setting unit 3, an ultrasonic data acquisition unit 4, a signal processing unit 6, a diagnostic image generation unit 7, and a storage unit 8.

The input unit 1 has a function for inputting a reference image and a hardware configuration and control parameter information that are associated with the reference image. In order to generate parameters to be used in the generation of a diagnostic image from the information associated with the reference image, the parameter setting unit 3 converts such information into a format that is in accordance with the configuration of hardware connected to the input unit 1, and sets such converted information as the parameters. The ultrasonic data acquisition unit 4 drives a probe 5 based on the parameters set by the parameter setting unit 3, and acquires ultrasonic data. With respect to the ultrasonic data acquired by the ultrasonic data acquisition unit 4 and subjected to predetermined processing by the signal processing unit 6, the diagnostic image generation unit 7 performs image processing based on the parameters set by the parameter setting unit 3, thereby generating a diagnostic image. The storage unit 8 stores the parameters set by the parameter setting unit 3 and the diagnostic image generated by the diagnostic image generation unit 7 in association with each other.

The following is a more detailed description of the functions of the various units in the ultrasonic diagnosis device having the above configuration.

The input unit 1 is a console including various types of operating means such as a keyboard, a mouse, operation buttons, and a track ball. The input unit 1 is used by an operator in order to operate the device and input, for example, an instruction to read a reference image and information associated with the reference image from a storage medium 2 that is described later, information related to an institution name, an examination date, a patient ID, an operator ID, an examination site, and the like, and modifications to device control parameters and image processing parameters.

The storage medium 2 is a storage medium such as a CD or a DVD and stores a reference image, information associated with the reference image, various types of statistical data, and the like, and stored information is read therefrom in accordance with an instruction made by the operator with use of the input unit 1.

The parameter setting unit 3 more specifically includes a parameter conversion unit 10, a first parameter setting unit 11, and a second parameter setting unit 12.

The parameter conversion unit 10 extracts parameters used in reference image acquisition from the information associated with the reference image that has been input, and classifies the individual extracted parameters into device control parameters and image processing parameters. The device control parameters are parameters for the acquisition of ultrasonic data, and the image processing parameters are parameters for generating a diagnostic image by performing image processing on acquired ultrasonic data.

The first parameter setting unit 11 sets, as device values, parameters such as a dynamic range, an acoustic power, a transmission power, an oscillation frequency and STC (Sensitive Time Control), which have been classified as device control parameters by the parameter conversion unit 10.

The second parameter setting unit 12 sets, as device values, parameters such as edge enhancement, a frame rate, and an imaging mode, which have been classified as image processing parameters by the parameter conversion unit 10.

Based on the device control parameters set by the first parameter setting unit 11, the ultrasonic data acquisition unit 4 acquires ultrasonic data by supplying a transmission signal to a plurality of oscillating elements that configure the below-described probe 5, and receiving an output signal from the oscillating elements.

The probe 5 is an ultrasonic probe that emits ultrasonic pulses onto a subject body from the ultrasonic oscillating elements, receives reflected ultrasonic waves from tissue in the body, and converts the reflected ultrasonic waves into an electrical signal. The probe 5 forms a scanning plane by scanning an ultrasonic beam formed by a plurality of array oscillating elements.

The signal processing unit 6 performs processing such as phasing and addition, detection, and logarithmic compression on the ultrasonic data acquired by the ultrasonic data acquisition unit 4.

Based on the data from the signal processing unit 6 and the image processing parameters that have been set by the second parameter setting unit 12, the diagnostic image generation unit 7 performs scan conversion with use of a digital scan converter, and performs brightness and contrast adjustment, image processing, and image synthesis with use of an image formatter.

The storage unit 8 stores the diagnostic image generated by the diagnostic image generation unit 7, the device control parameters used in diagnostic image acquisition, and the image processing parameters in association with each other. The storage unit 8 also can store various types of associated statistical data and the like in accordance with an instruction from the input unit 1. Furthermore, the storage unit 8 can readout stored information and copy and move stored information to the storage medium 2 in accordance with an instruction from the input unit 1.

A display unit 9 is used for displaying reference images, statistical data, newly acquired diagnostic images, and the like in accordance with an image signal supplied from the diagnostic image generation unit 7. For example, the display unit 9 can display a reference image and a newly acquired diagnostic image in parallel, independently, as enlarged, or the like in accordance with an instruction from the input unit 1.

Figure 2:
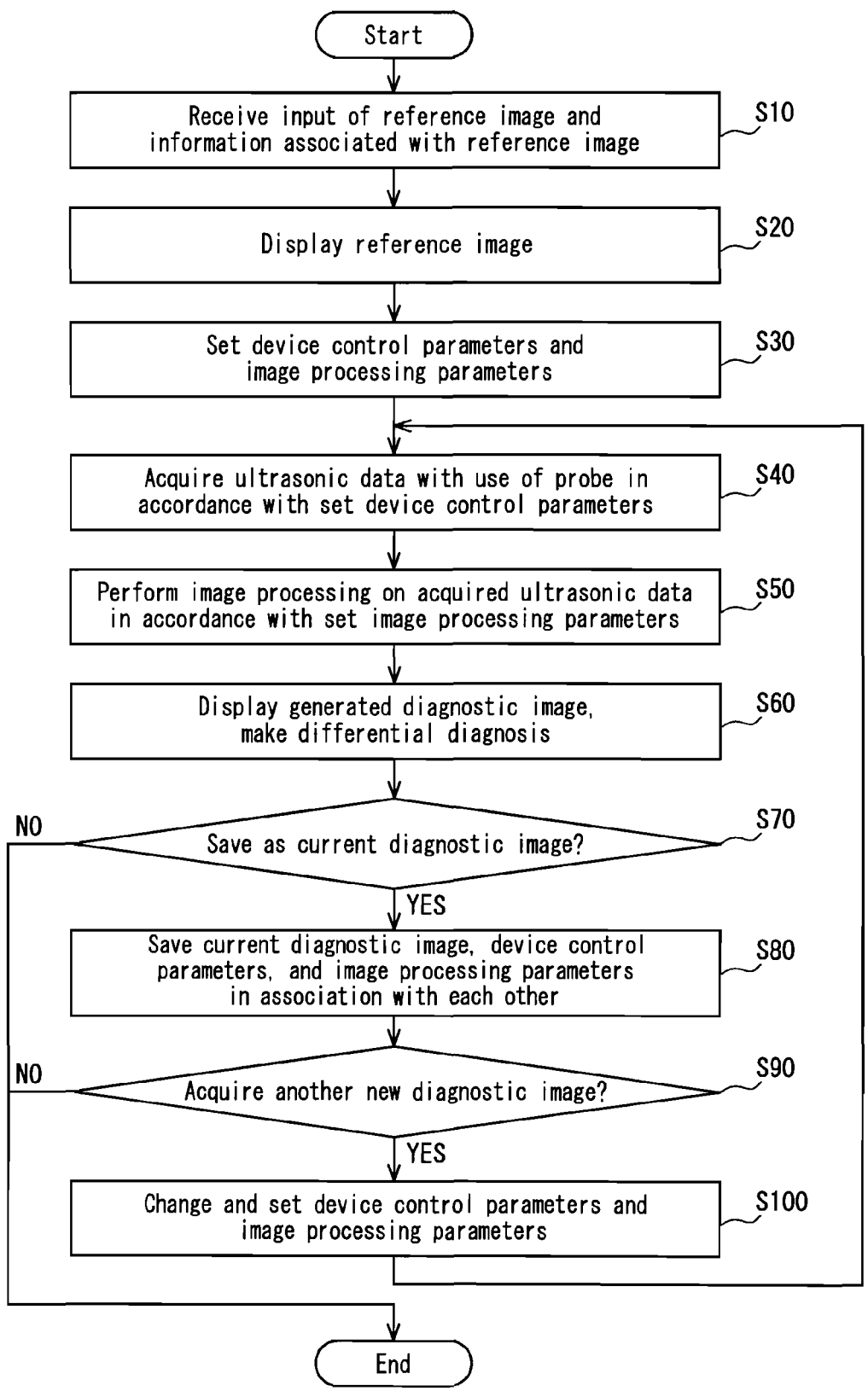
FIG. 2 is a flowchart showing operations performed by the ultrasonic diagnosis device according to Embodiment 1 of the present invention.

The following describes operations performed in the ultrasonic diagnosis device having the above configuration with reference to the flowchart of FIG. 2.

First, in step S10, the operator operates the keyboard or the like of the input unit 1 to input (read) a reference image and information associated with the reference image that are stored on the storage medium 2 such as a CD, a DVD, or the like, to the ultrasonic diagnosis device side.

The associated information are device control parameters such as a dynamic range, an acoustic power, a transmission power, an oscillation frequency STC, and the like, and image processing parameters such as edge enhancement, a frame rate, and the like, and are stored on the storage medium 2 such as a CD, a DVD, or the like, in association with the reference image.

Also, related information such as an institution name, an examination date, a patient ID, an operator ID, and an examination site are input as necessary. Next, the read reference image and part of the information associated with the reference image are displayed on the display unit 9 (S20).

Next, parameters used in reference image acquisition are extracted from the hardware configuration and control parameter information associated with the reference image that has been read. Then, the individual extracted parameters are classified into device control parameters for the acquisition of ultrasonic data, and image processing parameters for generating a diagnostic image by performing image processing on acquired ultrasonic data. At this time, the device control parameters are converted into a format that is in accordance with the hardware configuration. As a result of the above processing, the device control parameters and the image processing control parameters are set by the first parameter setting unit 11 and the second parameters setting unit 12 respectively in the ultrasonic diagnosis device that is to acquire the current diagnostic image (S30).

The probe 5 is driven in accordance with the set device control parameters, and ultrasonic data is acquired by the ultrasonic data acquisition unit 4 (S40). Next, signal processing such as phasing and adding processing, detection processing, and logarithmic compression processing is performed on the acquired ultrasonic data by the signal processing unit 6. The diagnostic image generation unit 7 performs scan conversion on the thus obtained signal with use of a digital scan converter and performs image processing on the thus obtained signal using an image formatter and with use of the set image processing parameters, thus generating a diagnostic image (S50).

Next, the display unit 9 displays, in parallel, the current diagnostic image that has been generated and the reference image that has been read in accordance with an instruction from the input unit 1, and a differential diagnosis, such as whether or how much temporal change has occurred in a lesion, is made (S60).

Next, a determination is made as to whether the current diagnostic image that has been generated is to be stored as a new diagnostic image (S70). Operations are ended if there has not been a temporal change in the lesion and there is no need to save the current diagnostic image as a new diagnostic image (S70: NO).

If the current diagnostic image that has been generated is to be saved (S70: YES) for a reason such as a temporal change in the lesion, or a lack of a temporal change in the lesion but a need for the diagnostic image to be saved as a history record, the current diagnostic image that has been generated, the device control parameters used in the current diagnostic image acquisition, and the image processing parameters are associated with each other and saved in the storage unit 8 (S80). At this time, related information such as an institution name, an imaging date, a subject body name, a subject body ID number, and an examination site, which have been input with use of the input unit 1 as necessary, is also associated with the current diagnostic image that has been generated and saved in the storage unit 8.

Next, a determination is made as to whether there is a need to acquire another new diagnostic image (S90), and if there has been no temporal change in the lesion and there is no need for a new diagnostic image (S90: NO), operations are ended.

If there is a need for another new diagnostic image (S90: YES) for a reason such as a temporal change in the lesion, or a change in the physique of the subject body since the previous time when imaging was performed, the keyboard and knobs, switches, and the like of the console of the input unit 1 are operated to set new numerical values for the device control parameters and the image processing parameters in order to acquire a new diagnostic image (S100). Thereafter, processing returns to step S40 in which the ultrasonic data acquisition unit 4 drives the probe 5 in accordance with the set device control parameters and acquires ultrasonic data.

Hereinafter, the above operations are repeated and a new diagnostic image is saved, or the operations are ended when there is no need for the acquisition of a new image.

As described above, according to the ultrasonic diagnosis device of the present embodiment, parameters used in reference image acquisition are extracted from a hardware configuration and control parameter information that are associated with a reference image that has been input. The individual extracted parameters are classified into device control parameters that have been converted into a format that is in accordance with the hardware configuration for acquiring ultrasonic data from a subject body, and image processing parameters for generating a diagnostic image by performing image processing on acquired ultrasonic data. Thus the device control parameters and the image processing parameters easily can be set so as to be the same as those of the reference image in the ultrasonic diagnosis device that is to acquire the current diagnostic image. Accordingly, the time required for performing setting is reduced regardless of the knowledge and experience of the operator, and it is possible to alleviate the burden on the operator.

Also, if the acquired current diagnostic image and the read reference image are displayed in parallel at the same image quality, it is possible objectively and easily to make a differential diagnosis as to whether or how much temporal change has occurred in a lesion, even if the skill, knowledge, experience, and the like of the operator are not superior.

Also, in addition to the acquired current diagnostic image and the device control parameters used in acquisition, changes in parameters caused by additional adjustment in the ultrasonic diagnosis device and the current hardware configuration are stored in association with the image processing parameters, thus enabling the stored information to be reused easily in the future.

Note that although the reference image is a previous diagnostic image of the same subject body and the same site in the above description, it is possible for diagnostic images of the same site in different subject bodies that are the same sex, in the same age group, and have a similar physique to be taken into account as reference images in the differential diagnosis.

Note that by classifying the individual extracted parameters into device control parameters for the acquisition of ultrasonic data and image processing parameters for generating a diagnostic image by performing image processing on the acquired ultrasonic data, even when data of an acquired current diagnostic image and read-out reference image (input from a storage medium or the like via an input device) are processed offline (e.g., by a personal computer), it is made possible to adjust the image and perform a diagnosis similarly to a condition where the ultrasonic diagnosis device itself exists, as well as when operating on the ultrasonic diagnosis device.

Embodiment 2

Figure 3:
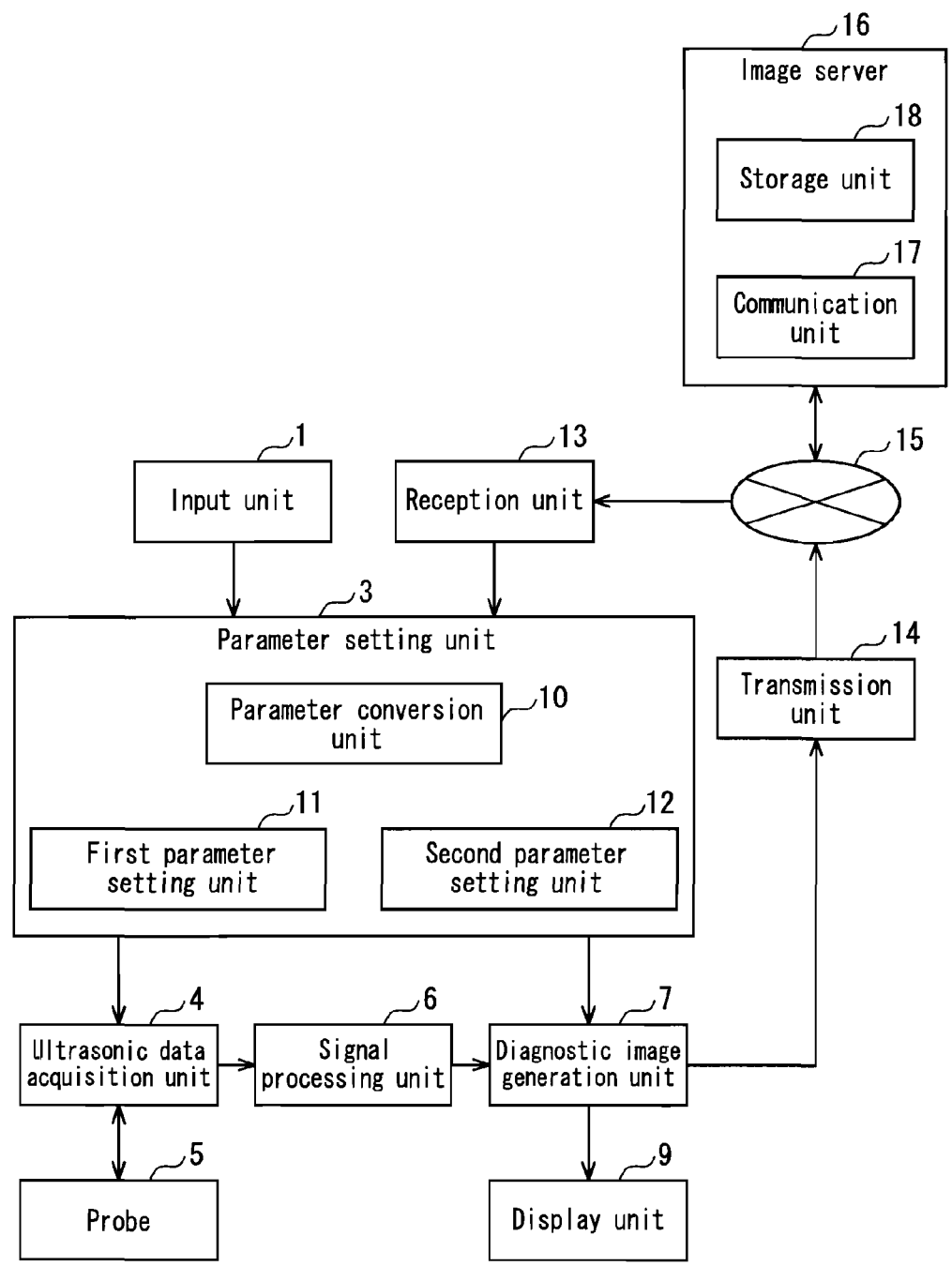
FIG. 3 is a block diagram showing a configuration of an ultrasonic diagnosis system according to Embodiment 2 of the present invention.

FIG. 3 is a block diagram showing a configuration of an ultrasonic diagnosis system according to Embodiment 2 of the present invention. This ultrasonic diagnosis system is composed of an ultrasonic diagnosis device that generates diagnostic images from ultrasonic data and an image server that is connected to the ultrasonic diagnosis device via a communication network. The ultrasonic diagnosis device has the configuration obtained by modifying partially the device in Embodiment 1. Accordingly, the same numerals are assigned to constituent elements that are the same as in Embodiment 1 shown in FIG. 1, and repetitive descriptions thereof will be partially omitted.

In FIG. 3, the ultrasonic diagnosis device includes a reception unit 13, the parameter setting unit 3, the ultrasonic data acquisition unit 4, the diagnostic image generation unit 7, and a transmission unit 14. An image server 16 includes a communication unit 17 that performs communication with the ultrasonic diagnosis device, and a storage unit 18 that stores information.

The configuration of this ultrasonic diagnosis device differs from that in Embodiment 1 shown in FIG. 1 with respect to the provision of the reception unit 13 and the transmission unit 14. The reception unit 13 has a function for receiving a reference image, a hardware configuration and control parameter information that are associated with the reference image. The transmission unit 14 has a function for transmitting a diagnostic image generated by the diagnostic image generation unit 7 in association with parameters set by the parameter setting unit 3, which has been caused to reflect changes in parameters caused by additional adjustment in the ultrasonic diagnosis device and the current hardware configuration.

Next is a description of the functions of the units that differ from Embodiment 1 in the ultrasonic diagnosis system having the above configuration.

The reception unit 13 receives a reference image, a hardware configuration associated with the reference image, control parameter information, and the like from the image server 16 via a communication network 15 in accordance with an instruction from the input unit 1.

In accordance with an instruction from the input unit 1, the transmission unit 14 transmits, to the below-described image server 16 via the communication network 15, a current diagnostic image that has been generated by the diagnostic image generation unit 7 in association with information including device control parameters used in current diagnostic image acquisition, which has been caused to reflect changes in parameters caused by additional adjustment in the ultrasonic diagnosis device and the current hardware configuration, and image processing parameters.

Via the communication network 15, the communication unit 17 that constitutes part of the image server 16 receives information that has been transmitted from the transmission unit 14 of the ultrasonic diagnosis device, and transmits information to the reception unit 13 of the ultrasonic diagnosis device.

The storage unit 18 stores reference images, information associated with the reference images, and information that has been received by the communication unit 17.

Figure 4:
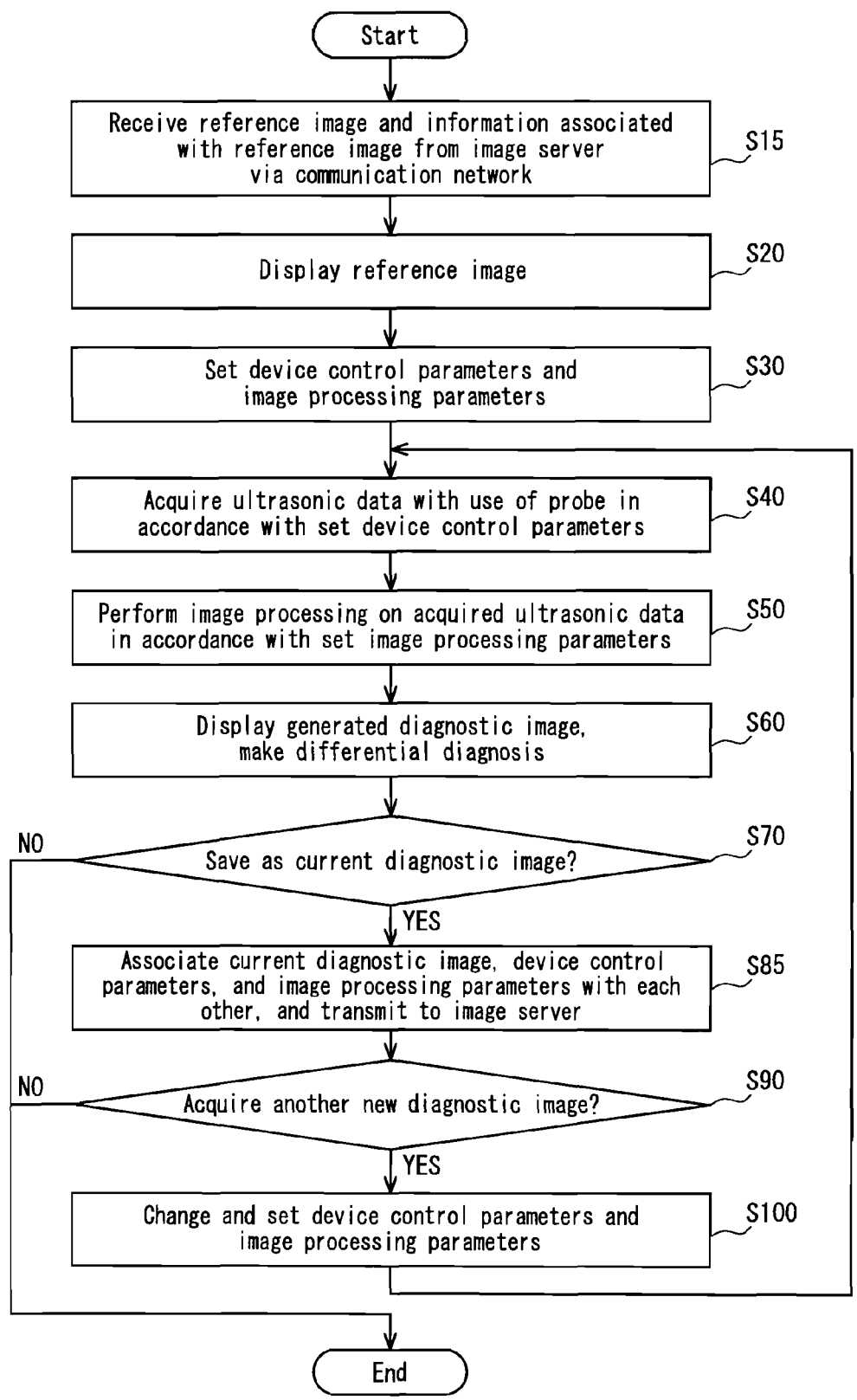
FIG. 4 is a flowchart showing operations performed in the ultrasonic diagnosis device system according to Embodiment 2 of the present invention.

The following describes operations performed in the ultrasonic diagnosis system having the above configuration with reference to the flowchart of FIG. 4. Note that the same reference numerals have been given to steps that are the same as those in the flowchart of FIG. 2 in Embodiment 1, and repetitive descriptions thereof have been partially omitted.

In FIG. 4, first the operator operates the keyboard and the like of the input 1, and a reference image and information associated with the reference image that are stored in image server 16 are received (S15). Also, related information such as an institution name, an examination date, a patient ID, an operator ID, and an examination site are input as necessary, and the received reference image and part of the information associated with the reference image are displayed on the display unit 9 (S20).

Thereafter, the operations from step S30 to step S60 are the same as the operations from step S30 to step S60 in the flowchart of FIG. 2, and therefore a description of these operations has been omitted.

Next, a determination is made as to whether the current diagnostic image that has been generated is to be stored as a new diagnostic image (S70). Operations are ended if there has not been a temporal change into the lesion and there is no need to save the current diagnostic image as a new diagnostic image (S70: NO).

If the current diagnostic image that has been generated is to be saved (S70: YES) for a reason such as a temporal change in the lesion, or a lack of a temporal change in the lesion but a need for the current diagnostic image to be saved as a history record, the current diagnostic image that has been generated is transmitted in association with the device control parameters used in the current diagnostic image acquisition and the image processing parameters by the transmission unit 14 to the image server 16 via the communication network 15, and then saved in the storage unit 18 (S85).

Also, related information such as an institution name, an imaging date, a subject body name, a subject body ID number, and an examination site, which have been input with use of the input unit 1 as necessary, also is saved in the storage unit 18 in association with the current diagnostic image that has been generated.

Next, a determination is made as to whether there is a need to acquire another new diagnostic image (S90), and if there has been no temporal change in the lesion and there is no need for a new diagnostic image (S90: NO), operations are ended.

If there is a need for another new diagnostic image (S90: YES) for a reason such as a temporal change in the lesion, or a change in the physique of the subject body since the previous time when imaging was performed, the keyboard and knobs, switches, and the like of the console of the input unit 1 are operated to set the device new control parameters and the image processing parameters in order to acquire a new diagnostic image (S100). Then, processing returns to step S40 in which the ultrasonic data acquisition unit 4 drives the probe 5 in accordance with the set device control parameters and acquires ultrasonic data.

Hereinafter, the above operations are repeated and a new diagnostic image is saved, or the operations are ended when there is no need for the acquisition of a new image.

As described above, according to the ultrasonic diagnosis system of the present embodiment, parameters used in the reference image acquisition are extracted from a hardware configuration and control parameter information that are associated with a reference image that has been input. The individual extracted parameters are classified into device control parameters that have been converted into a format that is in accordance with the hardware configuration for acquiring ultrasonic data from a subject body, and image processing parameters for generating a diagnostic image by performing image processing on acquired ultrasonic data. Thus the device control parameters and the image processing parameters easily can be set so as to be the same as those of the reference image in the ultrasonic diagnosis device that is to acquire the current diagnostic image. Accordingly, the time required for performing setting is reduced regardless of the knowledge and experience of the operator, and it is possible to alleviate the burden on the operator.

Also, if the acquired current diagnostic image and the read reference image are displayed in parallel at the same image quality, it is possible objectively and easily to make a differential diagnosis as to whether or how much temporal change has occurred in a lesion, even if the skill, knowledge, experience, and the like of the operator are not superior.

Also, the diagnostic image, the information associated with the diagnostic image, various types of statistical data and the like are saved in the image server, and therefore can be accessed by another ultrasonic diagnosis device or medical institution that is connected to the communication network and is authorized. Accordingly, the sharing and effective utilization of data are achieved, a differential diagnosis can be made by a medical specialist or specialized institution, and a more appropriate and advanced differential diagnosis can be made.

Note that although the reference image is a previous diagnostic image of the same subject body and the same site in the above description, it is possible for diagnostic images of the same site in different subject bodies that are the same sex, in the same age group, and have a similar physique to be taken into account as reference images in the differential diagnosis.

Embodiment 3

Figure 5:
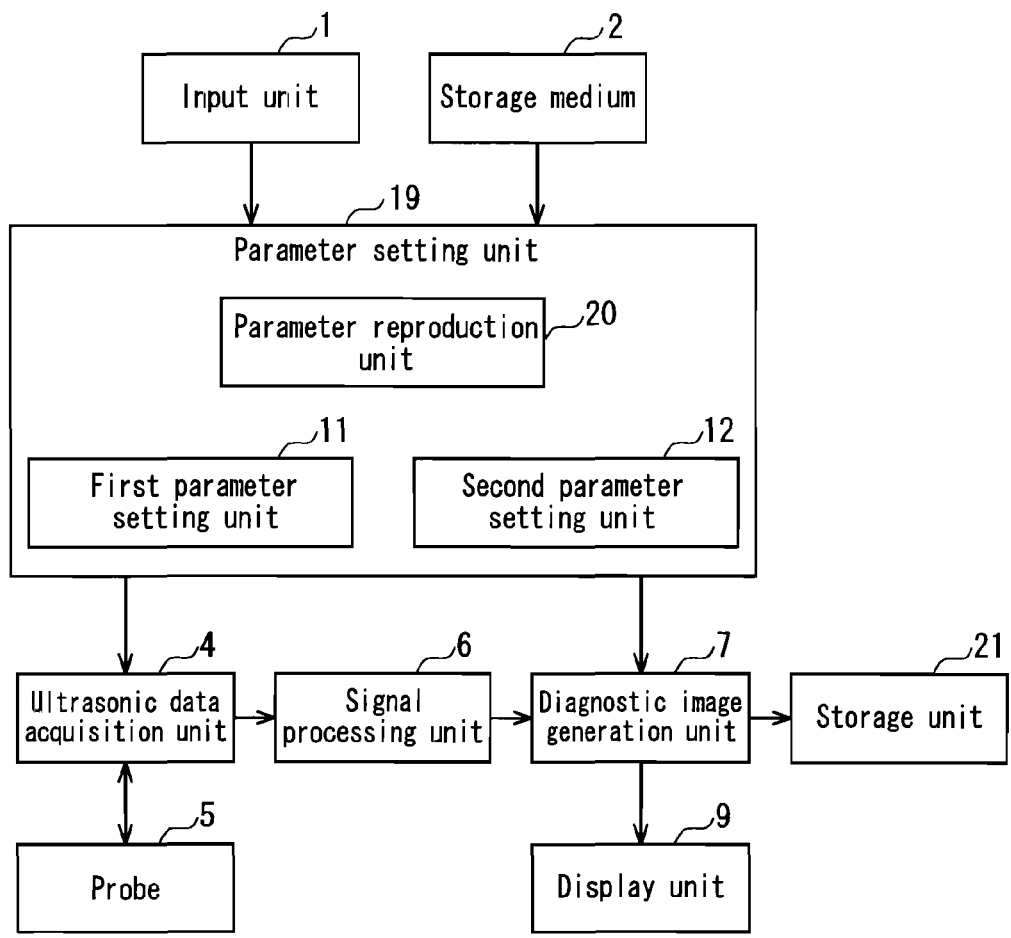
FIG. 5 is a block diagram showing a configuration of an ultrasonic diagnosis device according to Embodiment 3 of the present invention.

FIG. 5 is a block diagram showing a configuration of an ultrasonic diagnosis device according to Embodiment 3 of the present invention. The ultrasonic diagnosis device has the configuration obtained by modifying partially the device in Embodiment 1. Accordingly, the same numerals are assigned to constituent elements that are the same as in Embodiment 1 shown in FIG. 1, and repetitive descriptions thereof will be partially omitted.

The ultrasonic diagnosis device in FIG. 5 is composed of the input unit 1, a parameter setting unit 19, the ultrasonic data acquisition unit 4, the signal processing unit 6, the diagnostic image generation unit 7, and a storage unit 21. This ultrasonic diagnosis device differs from that in Embodiment 1 shown in FIG. 1 with respect to the parameter setting unit 19 and the function of the storage unit 21. For this reason, the data that is input from the input unit 1 differs from that in Embodiment 1.

Specifically, a reference image and "information associated with the reference image that has been converted (compiled) into control data in a certain protocol format not dependent on a hardware configuration" are input from the input unit 1. The parameter setting unit 19 has a function for, from among the information associated with the reference image that has been converted into control data in a certain protocol format, converting parameters to be used in the generation of a diagnostic image into a format that is in accordance with the hardware configuration of the ultrasonic diagnosis device in which the input unit 1 is included, thus reproducing and setting such parameters. The storage unit 21 has a function for storing a diagnostic image that has been generated by the diagnostic image generation unit 7, in association with the information relating to the reference image that has been re-converted into control data in a certain protocol format not dependent on the hardware configuration, which has been caused to reflect changes in parameters caused by additional adjustment in the ultrasonic diagnosis device.

Next is a description of the functions of the units that differ from Embodiment 1 in the ultrasonic diagnosis device having the above configuration.

The parameter setting unit 19 is composed of a parameter reproduction unit 20, the first parameter setting unit 11, and the second parameter setting unit 12. The parameter reproduction unit 20 reproduces the information associated with the reference image that has been converted into control data in a certain protocol format not dependent of the hardware configuration that has been input, and extracts, from the reproduced information, parameters that were converted into a format that is in accordance with the hardware configuration for reference image acquisition. Furthermore, the individual extracted parameters are classified into device control parameters for the acquisition of ultrasonic data, and image processing parameters for generating a diagnostic image by performing image processing on acquired ultrasonic data.

Here, the "control data in a certain protocol format not dependent on the hardware configuration" refers to an information set indicating processing procedure specifications (e.g., data alignment, number of bits, and specifications for responses between circuits and devices). Also, the "control data" has a format in which the device control parameters and the image processing parameters are aligned in accordance with a certain rule, and according to such format, various types of parameters and the like can be mutually exchanged even between models that have different hardware configurations, as long as the protocol format can be identified. Also, if the volume of data is large, conversion such as lossless compression furthermore may be performed to reduce the volume.

The storage unit 21 functions similarly to the storage unit 8 in FIG. 1, but stores the device control parameters used in diagnostic image acquisition and the image processing parameters to be stored in association with the diagnostic image as data on which lossless compression has been performed.

A description of the operations performed in the ultrasonic diagnosis device having the above configuration has been omitted since they are the same as those in the flowchart of FIG. 2.

As described above, according to the ultrasonic diagnosis device of the present embodiment, a reference image that has been input and information associated with the reference image that has been converted into control data in a certain protocol format not dependent on a hardware configuration are reproduced. Parameters used in reference image acquisition are extracted from the reproduced information associated with the reference image. The individual extracted parameters are classified into device control parameters that have been converted into a format that is in accordance with the hardware configuration for acquiring ultrasonic data from a subject body, and image processing parameters for generating a diagnostic image by performing image processing on acquired ultrasonic data. Thus the device control parameters and the image processing parameters can be easily set so as to be the same as those of the reference image in the ultrasonic diagnosis device that is to acquire the current diagnostic image. Accordingly, the time required for performing setting is reduced regardless of the knowledge and experience of the operator, and it is possible to alleviate the burden on the operator.

Also, if the acquired current diagnostic image and the read reference image are displayed in parallel at the same image quality, it is possible to objectively and easily make a differential diagnosis as to whether or how much temporal change has occurred in a lesion, even if the skill, knowledge, experience, and the like of the operator are not superior.

Also, lossless compression is performed on the device control parameters used in the current diagnostic image acquisition and the image processing parameters before they are stored, thereby enabling a reduction in the volume of data, as well as enabling full restoration into the data from before conversion since the conversion is lossless.

Note that although lossless conversion is performed on only the information associated with the reference information before storage, the present invention is not limited to this. A configuration in which lossy compression is performed on a reference image having a large volume of data is also possible, and it is possible to significantly reduce the volume of data by selectively using lossless compression and lossy compression depending on the type of data to be stored.

Embodiment 4

Figure 6:
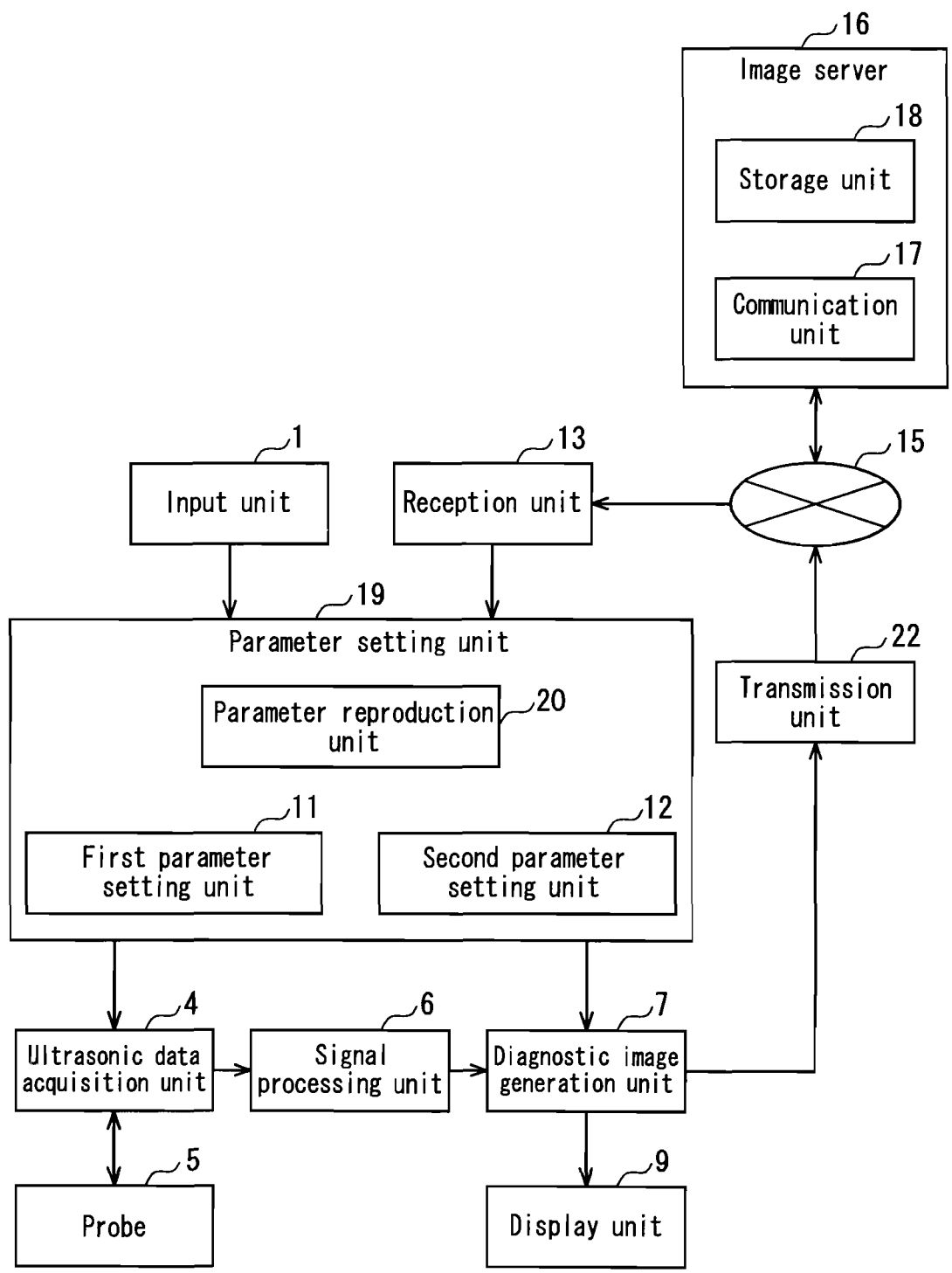
FIG. 6 is a block diagram showing a configuration of an ultrasonic diagnosis device according to Embodiment 4 of the present invention.
Figure 7:
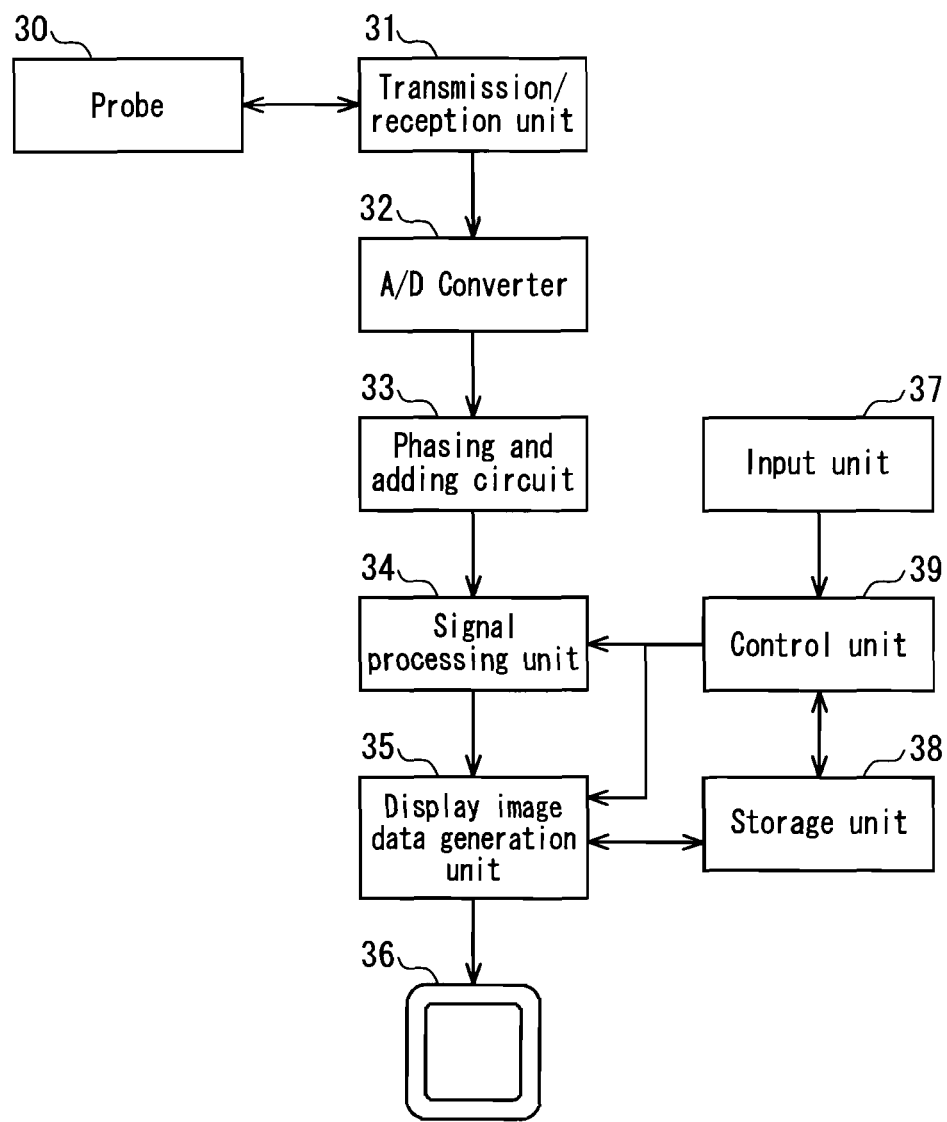
FIG. 7 is a block diagram showing a configuration of a conventional ultrasonic diagnosis device.

FIG. 6 is a block diagram showing a configuration of an ultrasonic diagnosis system according to Embodiment 4 of the present invention. The ultrasonic diagnosis system is composed of an ultrasonic diagnosis device that generates diagnostic images based on ultrasonic data and an image server that is connected to the ultrasonic diagnosis device via a communication network. This ultrasonic diagnosis system is obtained by modifying the ultrasonic diagnosis device in the system according to the configuration of Embodiment 2 shown in FIG. 3 in the same way as in Embodiment 3 shown in FIG. 5. Accordingly, the same numerals are assigned to constituent elements that are the same as those in the configurations shown in FIGS. 3 and 5, and repetitive descriptions thereof have been partially omitted.

As likewise with Embodiment 3, the reception unit 13 receives a reference image and information associated with the reference image that has been converted into control data in a certain protocol format not dependent on a hardware configuration. The parameter setting unit 19 includes the parameter reproduction unit 20 that reproduces the information associated with the reference image that has been converted into control data in a certain protocol format, the first parameter setting unit 11 that sets parameters reproduced by the parameter reproduction unit 20 as device control parameters that have been converted into a format that is in accordance with the hardware configuration, and the second parameter setting unit 12 that sets parameters reproduced by the parameter reproduction unit 20 as image processing parameters.

A transmission unit 22 has a function for transmitting a diagnostic image generated by the diagnostic image generation unit 7 in association with information relating to the diagnostic image that has been re-converted into control data in a certain protocol format not dependent on the hardware configuration, which has been caused to reflect changes in parameters caused by additional adjustment in the ultrasonic diagnosis device.

Next is a description of the function of the transmission unit 22, which is different from Embodiment 2 shown in FIG. 3 and Embodiment 3 shown in FIG. 5, in the ultrasonic diagnosis device having the above configuration.

The function of the transmission unit 22 is the same as that of the transmission unit 14 in FIG. 3, with the exception that the transmission unit 22 transmits, to the image server 16 via the communication network 15, data obtained by performing lossless compression on the device control parameters used in the diagnostic image acquisition and the image processing parameters that are to be associated with the diagnostic image and stored.

A description of the operations performed in the ultrasonic diagnosis system having the above configuration will be omitted since they are the same as those in the flowchart of FIG. 4.

As described above, according to the ultrasonic diagnosis device of the present embodiment, information associated with the reference image that has been converted into control data in a certain protocol format not dependent on the input hardware configuration is reproduced. Parameters used in reference image acquisition are extracted from the information associated with the reference image that has been reproduced. The individual extracted parameters are classified into device control parameters that have been converted into a format that is in accordance with the hardware configuration of the ultrasonic diagnosis device in which the reception unit is included for acquiring ultrasonic data from a subject body, and image processing parameters for generating a diagnostic image by performing image processing on the acquired ultrasonic data. Therefore, the device control parameters and the image processing parameters easily can be set so as to be the same as those of the reference image in the ultrasonic diagnosis device that is to acquire the current diagnostic image. Accordingly, the time required for performing setting is reduced regardless of the knowledge and experience of the operator, and it is possible to alleviate the burden on the operator.

Also, if the acquired current diagnostic image and the read reference image are displayed in parallel at the same image quality, it is possible objectively and easily to make a differential diagnosis as to whether or how much temporal change has occurred in a lesion, even if the skill, knowledge, experience, and the like of the operator are not superior.

Also, lossless compression is performed on the device control parameters used in the current diagnostic image acquisition and the image processing parameters before they are stored, thereby enabling a reduction in the volume of data, as well as enabling full restoration into the data from before conversion since the conversion is lossless.

Also, the diagnostic image, the information associated with the diagnostic image, various types of statistical data and the like are saved in the image server after lossless compression or lossy compression has been performed thereon. Therefore they can be accessed by another ultrasonic diagnosis device or medical institution that is connected to the communication network and is authorized. Thus, the sharing and effective utilization of data is achieved, a differential diagnosis can be made by a medical specialist or specialized institution, and a more appropriate and advanced differential diagnosis can be made.

Note that the information associated with the reference image is defined to be information converted into a predetermined format as necessary in view of the volume of data and the like as "control data in a certain protocol format not dependent on the hardware configuration". Thereby equivalent function and effects can be obtained in other devices that use the reference image thereafter, even if the hardware configurations thereof are different.

Industrial Applicability

An ultrasonic diagnosis device of the present invention is useful as an ultrasonic diagnosis device that, in the case of acquiring a new diagnostic image, enables easily setting device control parameters and image processing parameters so as to be the same as those of a reference image, and has a function for comparing new and old diagnostic images.

Also, according to an ultrasonic diagnosis device of the present invention, a reference image and device control parameters can be shared between device models having different configurations. Therefore the ultrasonic diagnosis device of the present invention is useful when a reference image whose set parameters have been adjusted finely by a specialist who has taken his/her time and who is well-versed in ultrasonic diagnosis has been made available, because the same parameter settings as those set by the preeminent specialist can be immediately reproduced even by an operator whose skill, knowledge, experience, and the like in ultrasonic diagnosis are not superior.

The invention claimed is:

1. An ultrasonic diagnosis device comprising:
  a diagnostic image generation unit that generates an ultrasonic image from ultrasonic data obtained by transmission and reception of ultrasonic waves;
  an input unit for receiving an input of data to be used by the diagnostic image generation unit;
  a parameter setting unit that sets parameter information necessary for acquiring the ultrasonic data and generating the ultrasonic image based on the input data that has been input;
  a storage unit that stores the ultrasonic image; and
  an ultrasonic data acquisition unit that, when a reference image with which parameter information is associated is input from the input unit, acquires the ultrasonic data based on the input parameter information,
  wherein the parameter setting unit comprises a first parameter setting unit that sets a device control parameter based on information associated with the ultrasonic image stored in the storage unit, and a second parameter setting unit that sets an image processing parameter based on the information associated with the ultrasonic image stored in the storage unit,
  the parameter setting unit adds hardware configuration information pertaining to the ultrasonic diagnosis device to the parameter information, in which the hardware configuration information is defined as information for converting the parameter information into a format that is in accordance with a hardware configuration of the current ultrasonic diagnosis device,
  the storage unit stores the parameter information in association with the ultrasonic image, with the hardware configuration information being added to the parameter information,
  the ultrasonic data acquisition unit acquires the ultrasonic data based on the device control parameter set by the first parameter setting unit,
  the diagnostic image generation unit generates a diagnostic image by, based on the image processing parameter set by the second parameter setting unit, performing image processing on the ultrasonic data acquired by the ultrasonic data acquisition unit, and
  the storage unit converts a change in parameter information caused by additional adjustment into a format conforming to the hardware configuration information of the ultrasonic diagnosis device, adds the resulting information to the device control parameter set by the first parameter setting unit, and stores the resulting device control parameter and the image processing parameter set by the second parameter setting unit, in association with the diagnostic image generated by the diagnostic image generation unit.

2. The ultrasonic diagnosis device according to claim 1, wherein when the ultrasonic image associated with the parameter information to which the hardware configuration information has been added are input from the input unit, the parameter setting unit converts the input parameter information into parameter information that is in accordance with the hardware configuration of the ultrasonic diagnosis device.

3. The ultrasonic diagnosis device according to claim 2, wherein the storage unit converts a change in the parameter information caused by additional adjustment into a format conforming to the hardware configuration information of the ultrasonic diagnosis device, adds the resulting information to the parameter information set by the parameter setting unit, and stores the resulting parameter information in association with the ultrasonic image generated by the diagnostic image generation unit.

4. An ultrasonic diagnosis system comprising an ultrasonic diagnosis device that generates an ultrasonic image from the ultrasonic data, and an image server that is connected to the ultrasonic diagnosis device via a communication network,
  the ultrasonic diagnosis device comprising:
  a reception unit that receives, from the image server, a hardware configuration information and parameter information that are associated with an ultrasonic image stored in the image server, in which the hardware configuration information is defined as information for converting the parameter information into a format that is in accordance with a hardware configuration of the current ultrasonic diagnosis device;
  a parameter setting unit that sets parameter information that has been converted into a format that is in accordance with the hardware configuration information of the ultrasonic diagnosis device based on the hardware configuration information and the parameter information;
  an ultrasonic data acquisition unit that acquires ultrasonic data based on the parameter information set by the parameter setting unit;
  a diagnostic image generation unit that generates the ultrasonic image by, based on the parameter information set by the parameter setting unit, performing image processing on the ultrasonic data acquired by the ultrasonic data acquisition unit; and
  a transmission unit that converts a change in the parameter information caused by additional adjustment into a format conforming to the hardware configuration information of the ultrasonic diagnosis device, adds the resulting information to the parameter information set by the parameter setting unit, and transmits the resulting parameter information in association with the diagnostic image generated by the diagnostic image generation unit, and the image server comprising:

a communication unit that performs communication with the ultrasonic diagnosis device; and a storage unit that stores information.

* * * * *